United States Patent [19]
Tanokura et al.

[11] Patent Number: 5,135,646
[45] Date of Patent: Aug. 4, 1992

[54] LIQUID SEPARATOR

[75] Inventors: Nobukazu Tanokura; Susumu Kobayashi, both of Fujinomiya; Akihiko Furuya, Fuji; Fumiaki Inaba, Fujinomiya, all of Japan

[73] Assignee: Terumo Kabushiki Kaisha, Tokyo, Japan

[21] Appl. No.: 551,941

[22] Filed: Jul. 12, 1990

[30] Foreign Application Priority Data

Jul. 14, 1989 [JP] Japan .................. 1-183500

[51] Int. Cl.⁵ .............................. B01D 21/30
[52] U.S. Cl. ...................... 210/109; 210/86; 210/94; 210/143; 210/513; 222/23; 222/52; 222/95; 222/96; 222/103; 222/214
[58] Field of Search .......... 210/86, 94, 109, 143, 210/513, 97; 222/23, 52, 95, 96, 103, 214

[56] References Cited

U.S. PATENT DOCUMENTS

| | | | |
|---|---|---|---|
| 4,350,585 | 9/1982 | Johansson et al. | 210/94 |
| 4,663,032 | 5/1987 | Loos et al. | 210/513 |
| 4,976,851 | 12/1990 | Tanokura et al. | 210/94 |
| 5,045,185 | 9/1991 | Ohnaka et al. | 210/86 |
| 5,061,451 | 10/1991 | Gänshirt et al. | 210/86 |

FOREIGN PATENT DOCUMENTS 57-30507 6/1982 Japan .
60-148562 8/1985 Japan .
63-47471 9/1988 Japan .

Primary Examiner—Robert A. Dawson
Assistant Examiner—Sun Uk Kim
Attorney, Agent, or Firm—Frishauf, Holtz, Goodman & Woodward

[57] ABSTRACT

A liquid separator of the present invention comprises a first plate member, a second plate member forming a receiving portion between it and the first plate member for receiving a flexible liquid container including liquid separated into the upper liquid layer and the lower liquid layer, and pushing means for pushing the second plate member toward the first plate member, said pushing means automatically pushing the second plate member with gradually decreasing pressure after starting the discharge of the upper liquid layer from the flexible liquid container. Therefore, the upper liquid layer can be discharged from the flexible liquid container without disturbing the boundary between the upper and lower liquid layers in the flexible liquid container. Thus, the upper liquid layer can automatically and efficiently be taken out from the flexible liquid container without mixing with the lower liquid layer and without any complicated and troublesome manipulation. If the discharge of the upper liquid layer is automatically stopped with a sensor detecting the boundary between the upper and lower liquid layers, it is possible to decrease errors of the sensor caused by the disturbance of the boundary.

16 Claims, 9 Drawing Sheets

PRIOR ART

LIQUID SEPARATOR

BACKGROUND OF THE INVENTION

This invention relates to a liquid separator for separating upper and lower liquid layers from each other stored in a flexible container. More particularly, it relates to a liquid separator for separating various blood portions or components such as blood plasma, red cells, etc. from blood stored in a flexible container such as a blood bag or the like.

In recent years, component transfusion in which only a blood component required by a patient is transfused to the patient has been employed instead of whole blood transfusion. On the other hand, blood plasma is collected for producing plasma preparations.

A blood bag system so-called "multibag" in which bags are connected to each other by tubes is used for blood component transfusion or preparing blood preparations. In such a blood bag system, blood stored in a blood collection bag (main bag) is separated into plasma component layer at the upper layer and blood cell component layer at the lower layer by centrifugation. The separated plasma component should be taken out without mixing with the blood cell component.

For this purpose, there are known liquid separators, for example, disclosed in Japanese Patent Publication Nos. Sho 57-30507 and Sho 63-47471.

Figure 9:
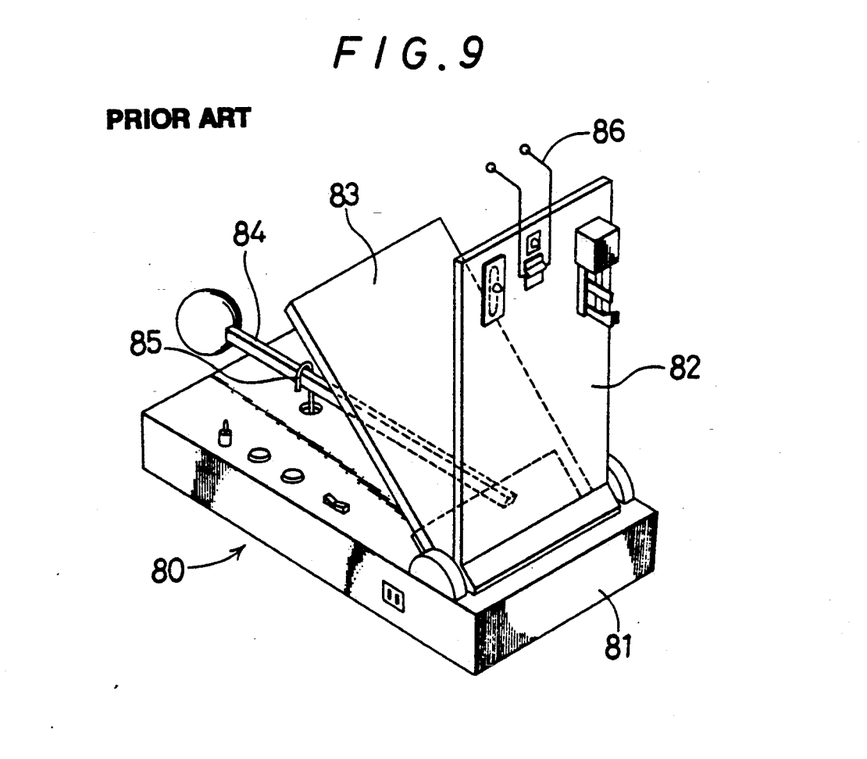
FIGS. 9 and 10 are views of prior art liquid separators.

As shown in FIG. 9, the liquid separator 80 disclosed in the Japanese Patent Publication No. Sho 57-30507 comprises a box base 81, a wall plate 82 perpendicularly mounted on the box base 81, a separator plate 83 pivotally supported on the box base 81 and movable toward the wall plate 82, a lever 84 for pushing the separator plate 83, and a hook 85 for the lever 84. The wall plate 82 is provided with a hanger 86 for hanging a blood bag. A blood bag after centrifugation is hung by the hanger 86 of the wall plate 82 and the lever 84 is then moved upward to sandwich the blood bag between the separator plate 83 and the wall plate 82. The blood bag is pressed by the separator plate 83 and the wall plate 82 so that plasma component of the upper layer of blood in the blood bag is discharged through a tube connected to the blood bag.

Figure 10:
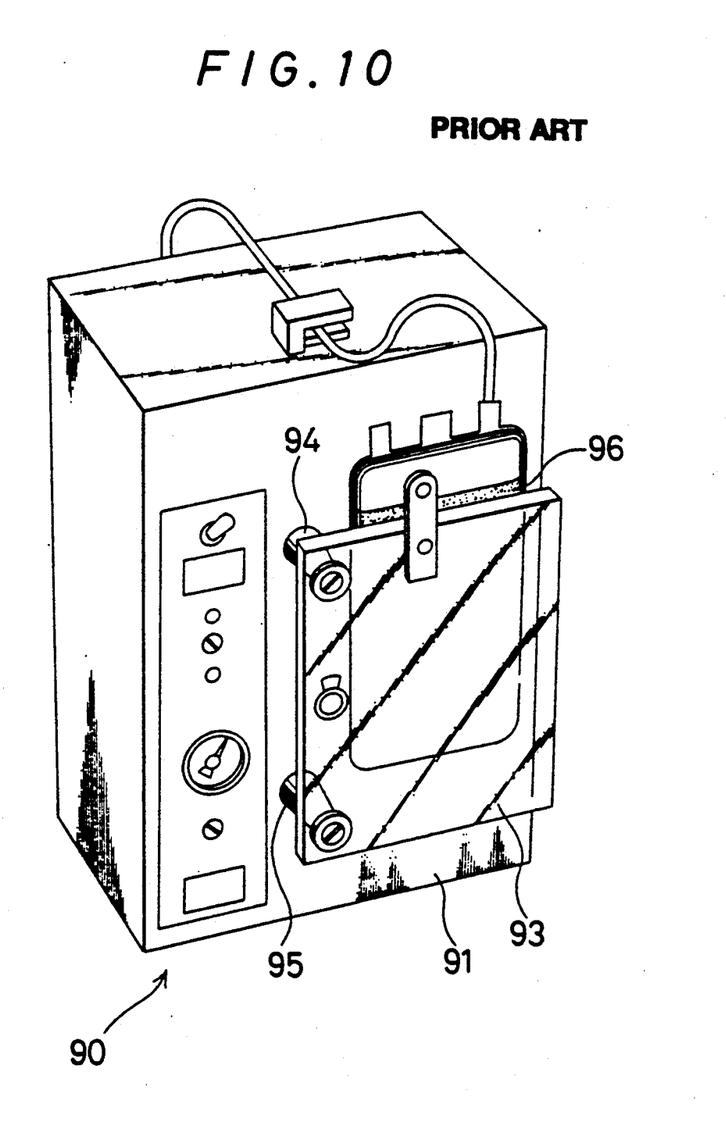

As shown in FIG. 10, the liquid separator 90 disclosed in the Japanese Patent Publication No. Sho 63-47471 comprises a side wall 91 of a box case 2, connecting rods 94 and 95 and a pressing plate 93 arranged parallelly with the side wall 91. The pressing plate 93 can be moved toward the side wall 91 by the connecting rods 94 and 95. A blood bag 96 after centrifugation is sandwiched between the side wall 91 and the pressing plate 93 and pressed by the pressing plate 93 so that blood in the blood bag 96 is discharged.

Plasma component separated from blood cell component in a blood bag should be taken out from the blood bag without mixing with the blood cell component and with good efficiency.

In the liquid separator 80 disclosed in the Japanese Patent Publication No. Sho 57-30507, the blood bag is pressed by manipulating the lever 84. However, a delicate manipulation of the lever 84 is required in order not to disturb the boundary between the plasma component and the blood cell component in the blood bag. Such a delicate manipulation was hard.

In the liquid separator 90 disclosed in the Japanese Patent Publication No. Sho 63-47471, the blood bag 96 is automatically pressed. The pressure for the blood bag 96 is fixed or increased at the end of the pressurization. In this liquid separator 90, however, there is the high possibility that the boundary between the plasma component and the blood cell component in the blood bag is disturbed and both are mixed with each other. Mixing of the components obstructs the accurate operation of a sensor for detecting the boundary between the components.

SUMMARY OF THE INVENTION

Accordingly, it is an object of the present invention to provide a liquid separator in which the upper liquid layer (for example, blood plasma component) separated from the lower liquid layer (for example, blood cell component) in a blood bag or the like can be automatically discharged from the blood bag or the like without disturbing the boundary between the upper and lower liquid layers and mixing the upper liquid layer with the lower liquid layer and without any complicated and troublesome manipulation.

The above object is attained by a liquid separator comprising a first plate member, a second plate member forming a receiving portion between it and said first plate member for receiving a flexible liquid container including liquid separated into the upper liquid layer and the lower liquid layer, and pushing means for pushing said second plate member toward said first plate member, said pushing means automatically pushing said second plate member with gradually decreasing pressure after starting the discharge of said upper liquid layer from said flexible liquid container.

The above object is also attained by a liquid separator comprising a first plate member, a second plate member forming a receiving portion between it and said first plate member for receiving a flexible liquid container including liquid separated into the upper liquid layer and the lower liquid layer, and pushing means for pushing said second plate member toward said first plate member, said pushing means automatically pushing said second plate member at gradually decreasing speed after starting the discharge of said upper liquid layer from said flexible liquid container.

DETAILED DESCRIPTION OF THE PREFERRED EMBODIMENTS

The liquid separator of the present invention will be described with reference to embodiments shown in the drawings.

Figure 1:
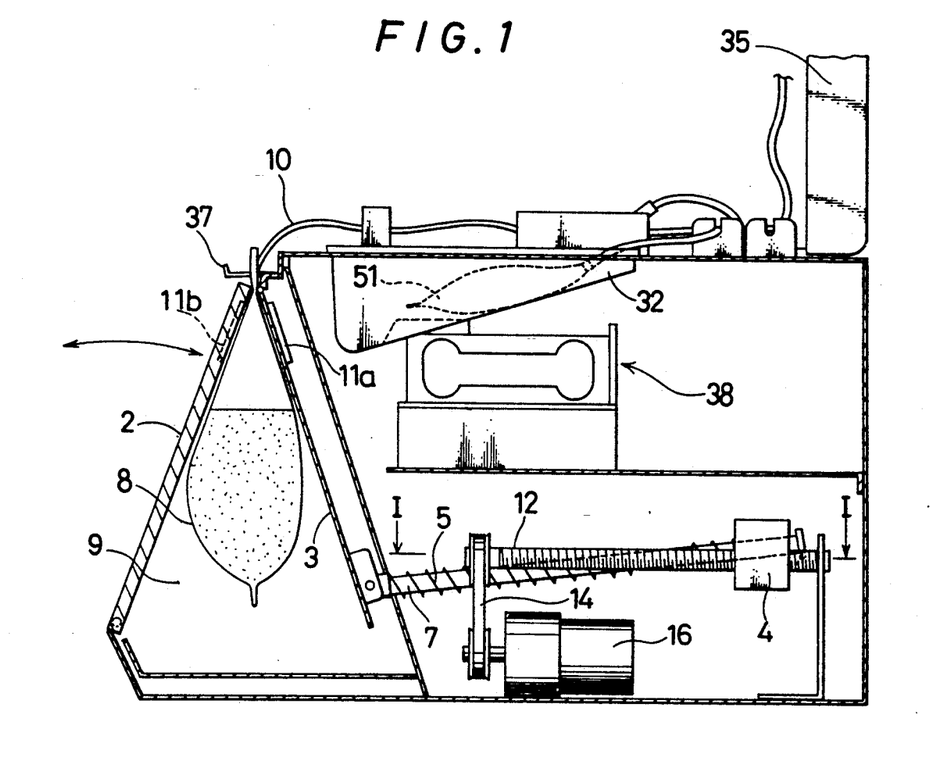
FIG. 1 is a schematic cross sectional view of a liquid separator according to one embodiment of the present invention.

The liquid separator 1 of the present invention comprises a first plate member 2, a second plate member 3 forming a receiving portion 9 between it and the first plate member 2 for receiving a flexible liquid container 8 including liquid separated into the upper liquid layer and the lower liquid layer, and pushing means for pushing the second plate member 3 toward the first plate member 2, said pushing means automatically pushing the second plate member 3 with gradually decreasing pressure after starting the discharge of the upper liquid layer from the flexible liquid container 8.

Figure 2:
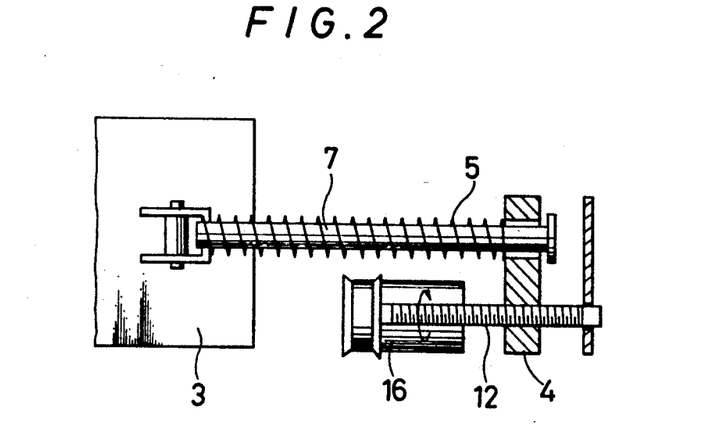
FIG. 2 is a cross section taken along line I—I of FIG. 1.
Figure 3A:
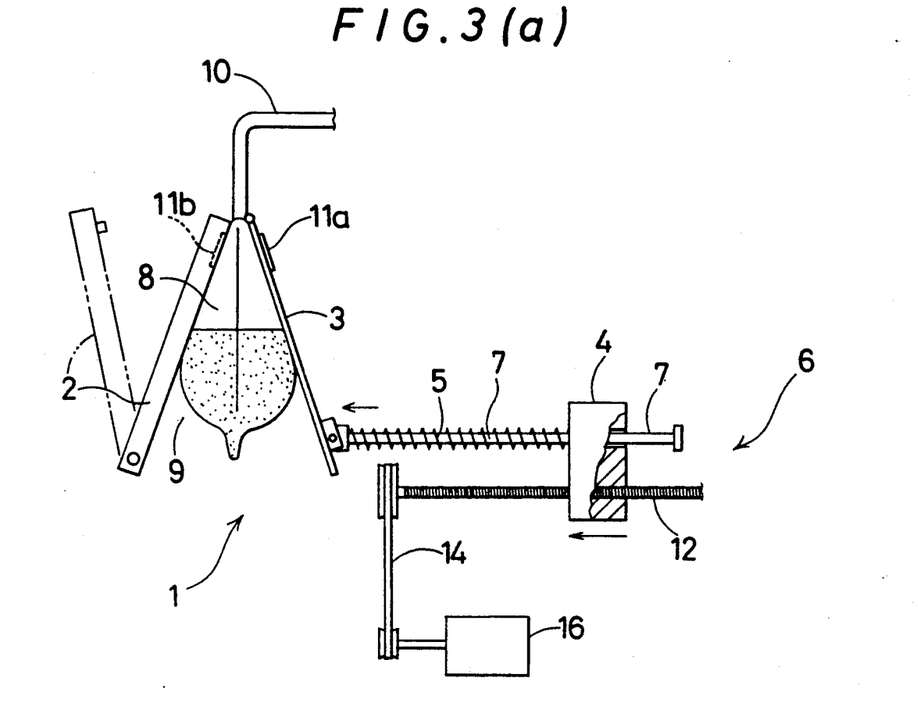
FIGS. 3(a) through 3(c) are views illustrating the operation of the liquid separator of the present invention.
Figure 3B:
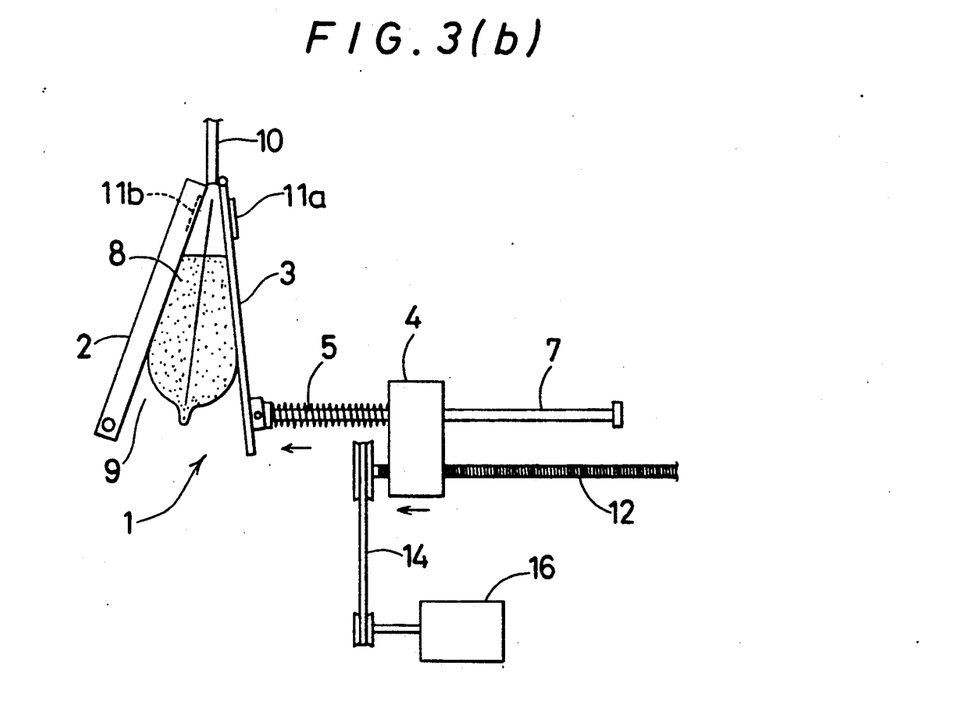

An embodiment in which the liquid separator 1 of the present invention is applied to a blood separator will be described with reference to FIGS. 1 through 3.

FIG. 1 is a schematic cross sectional view of the liquid separator 1 of the present invention. FIG. 2 is a cross section taken along line I—I of FIG. 1. FIGS. 3(a) through 3(c) are views illustrating the operation of the liquid separator 1 of the present invention.

The liquid separator 1 comprises a first plate member 2, a second plate member 3 forming a receiving portion 9 between it and the first plate member 2 for receiving a flexible liquid container 8 including liquid separated into the upper liquid layer and the lower liquid layer, and pushing means for pushing the second plate member 3 toward the first plate member 2. The pushing means comprises a pushing member 4, a spring member 5 disposed between the pushing member 4 and the second plate member 3, a shaft member 7 inserted in the spring member 5 and movably penetrating the pushing member 4, and drive means 6 for driving the pushing member 4 toward the second plate member 3. The second plate member 3 is pushed through the spring member 5.

The first plate member 2 is pivotally supported at its bottom portion. It is rotatable from a position shown by broken lines in FIG. 3(a) to a position shown by solid lines. It is fixed at the position shown by the solid lines after the liquid container 8 is received in the receiving portion 9. The second plate member 3 is pivotally supported at its upper end portion. It is rotatable toward the first plate member 2. Although the first and second plate members 2 and 3 are preferably flat, they may moderately be curved.

The drive means 6 comprises an electric motor 16 and transmitting means 14 for transmitting the torque of the motor 16 to a rotational shaft 12. The rotational shaft 12 is rotated to move the pushing member 4 toward the second plate member 3 as shown in FIG. 2 and FIGS. 3(a) through 3(c). The pushing member 4 is movably penetrated by the shaft member 7. The shaft member 7 extending between the pushing member 4 and the second plate member 3 is provided with the spring member 5. In this arrangement, when the pushing member 4 is moved toward the second plate member 3, it pushes the rear end of the spring member 5. The front end of the spring member 5 then pushes the second plate member 3 and the spring member 5 is compressed between the pushing member 4 and the second plate member 3. The shaft member 7 preferably advances in accordance with the compression of the spring member 5. For this purpose, the spring member 5 is wound on the shaft member 7 without looseness. If the spring member 5 is not curved, the shaft member 7 may not be disposed. The liquid container 8 compressed by the first and second plate members 2 and 3 is, for example, a blood bag provided with a tube 10 at its upper end. Blood in the blood bag has been separated into plasma component at the upper liquid layer and blood cell component at the lower liquid layer by centrifugation.

The operation of the liquid separator 1 will be described with reference to FIGS. 3(a) through 3(c). FIG. 3(a) shows the state in which the centrifuged blood bag is attached to the liquid separator 1. The drive means 6 is then operated to move the pushing member 4 toward the second plate member 3 as shown in FIG. 3(b). The spring member 5 then pushes the second plate member 3 and is compressed as shown in FIG. 3(b). The drive means 6 is stopped when the pushing member 4 reaches a predetermined position. In any case, however, it has been determined such that liquid flows out from the liquid container 8 through the tube 10 due to the compression by the first and second plate members 2 and 3 when the pushing member 4 is at the predetermined position. More specifically, it is generally determined to the position at which about 90% of the upper liquid layer (if the percentage of the upper liquid layer is 50% of the whole amount of the liquid, it is about 45% of the whole amount of the liquid) has flowed out from the liquid container 8. FIG. 3(b) shows the state in which the drive means 6 is stopped. The spring member 5 which has been compressed by the pushing member 4 and the second plate member 3 pushes the second plate member 3 by its restoring force as shown in FIG. 3(c). Because the restoring force gradually decreases, it is possible to discharge the upper liquid layer from the liquid container 8 through the tube 10 without disturbing the boundary between the upper and lower liquid layers in the liquid container 8. By using the spring member 5 for pushing the second plate member 3, the pushing force gradually decreases after the upper liquid layer starts to flow out of the liquid container 8. Therefore, the upper liquid layer can be discharged from the liquid container 8 through the tube 10 without disturbing the boundary between the upper and lower liquid layers in the liquid container 8. The second and first plate members 3 and 2 are provided with liquid detecting means 11a and 11b for detecting the lower liquid layer. On the basis of the detection of the lower liquid layer (the boundary between the upper and lower liquid layers) by the detecting means 11a and 11b, closing means (not shown) is operated to close the tube 10, completing the liquid separation operation. The detecting means 11a and 11b may consist of an optical sensor comprising a light emitting element and a light receiving element or an ultrasonic sensor comprising a transmitting element and a receiving element. The drive means for driving the pushing member 4 is not limited to the electric motor as described above but it may consist of an air cylinder or a hydraulic cylinder.

In the liquid separator of the present invention, there is used automatic drive means as described above. Therefore, any complicated and troublesome manipulation is not required and the upper liquid layer in the liquid container can be easily taken out.

Figure 3C:
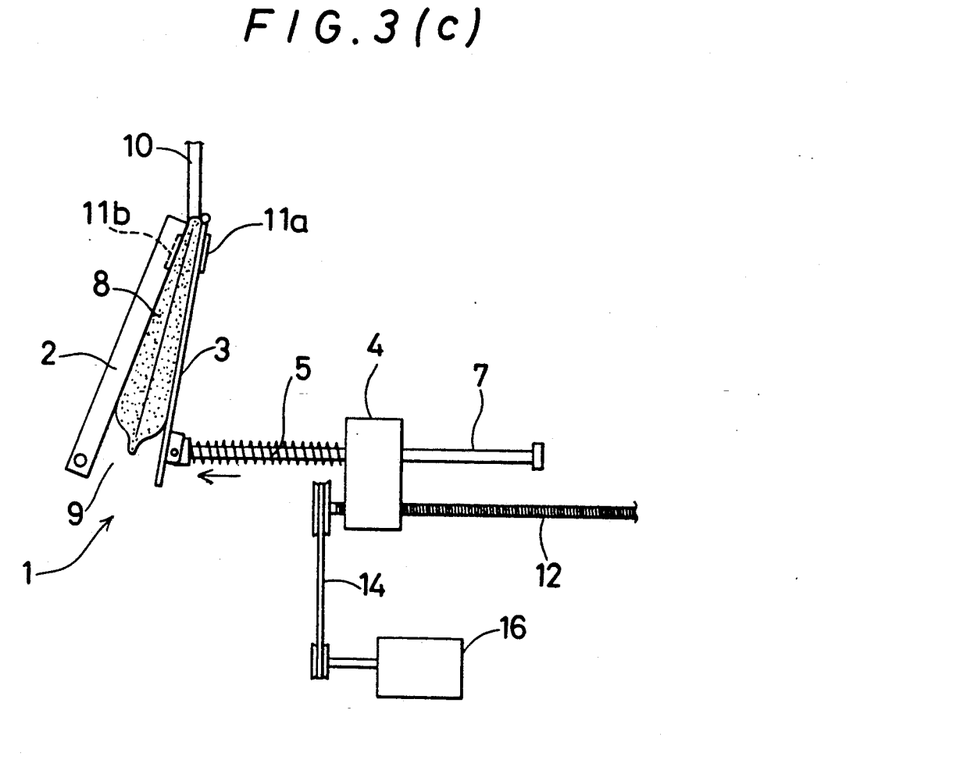
Figure 11A:
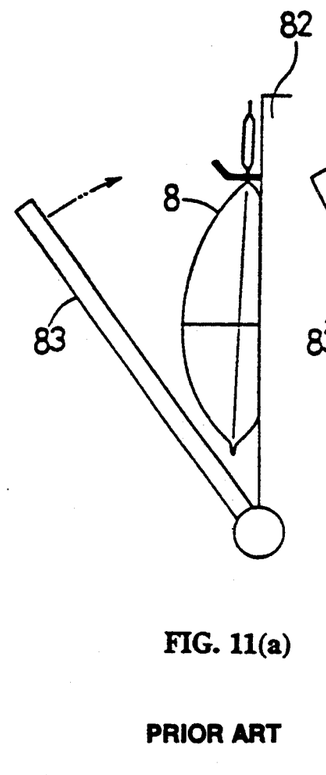
FIGS. 11(a)–11(c) are views illustrating the operation of the prior art liquid separator of FIG. 9.
Figure 11B:
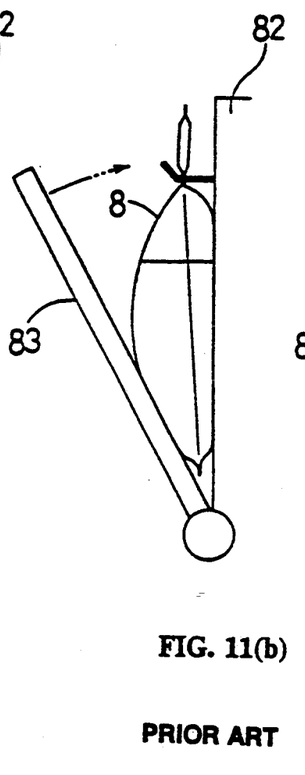
Figure 11C:
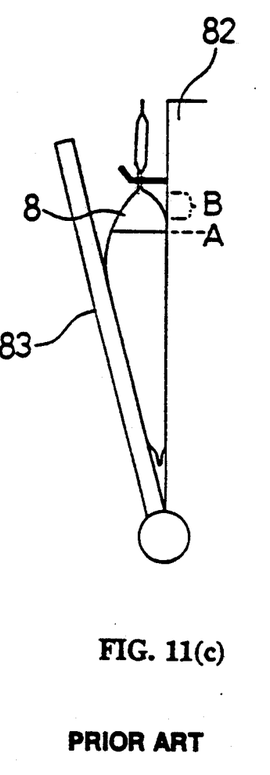

In the liquid separator 1 of this embodiment, when the first plate member 2 is at the position shown by the solid lines, the second plate member 3 is at the position at which the upper end of the second plate member 3 is near the upper end of the first plate member 2 as shown in FIG. 1 and FIGS. 3(a) through 3(c). The second plate member 3 is pivotally supported at its upper end portion and rotatable toward the first plate member 2. Therefore, the liquid container 8 is compressed by the rotation of the second plate member 3 from the upper portion of the liquid container 8 to the lower portion thereof. As the second plate member 3 is rotated, the space provided between the upper parts of the first and second plate members 2 and 3 is decreased as shown in FIG. 3(c). Accordingly, the amount of the upper liquid layer remaining in the liquid container 8 becomes little. Contrast to this, in the prior art liquid separator 80 shown in FIG. 9, the liquid container 8 is compressed from the lower portion to the upper portion as shown in FIGS. 11(a)-11(c). Thus, when rotating the separator plate 83, the upper portion of the liquid container 8 has a portion B which never come into contact with the wall plate 82. Accordingly, the boundary between the upper and lower liquid layers in the liquid container 8 can be detected only at a level A lower than the portion B. Thus, because the boundary can not be detected at a level near the upper end of the liquid container 8, the efficiency of taking out the upper liquid layer is bad. Besides, in this prior art liquid separator 80, when the liquid container 8 is compressed by the wall plate 82 and the separator plate 83, the upper portion of the liquid container 8 is expanded. Therefore, the amount of the upper liquid layer remaining in the liquid container 8 becomes much, lowering the efficiency of taking out the upper liquid layer. Furthermore, in this prior art liquid separator 80, because the liquid container 8 is compressed from the lower portion to the upper portion, there is the possibility that the liquid container 8 is lifted up when advancing the compression. Thus, it is difficult to set the level of an automatic boundary detection.

Contrast to this, in the liquid separator 1 of this embodiment, the whole of the upper portion of the liquid container 8 comes into close contact with the first and second plate members 2 and 3. Therefore, in the upper end portion of the liquid container 8, there is formed no portion which does not come into contact with the second plate member 3. Accordingly, it becomes possible to detect the boundary between the upper and lower liquid layers in the liquid container 8 at a higher level. Further, when the liquid container 8 is compressed by the first and second plate members 2 and 3, the upper portion of the liquid container 8 becomes flat. Thus, the amount of the upper liquid layer remaining in the liquid container 8 is little, resulting a good efficiency of taking out the upper liquid layer. Furthermore, because there is no possibility that the liquid container 8 is lifted up because the liquid container 8 comes into close contact with the first and second plate members 2 and 3, it is easy to set the level of an automatic boundary detection.

Figure 4:
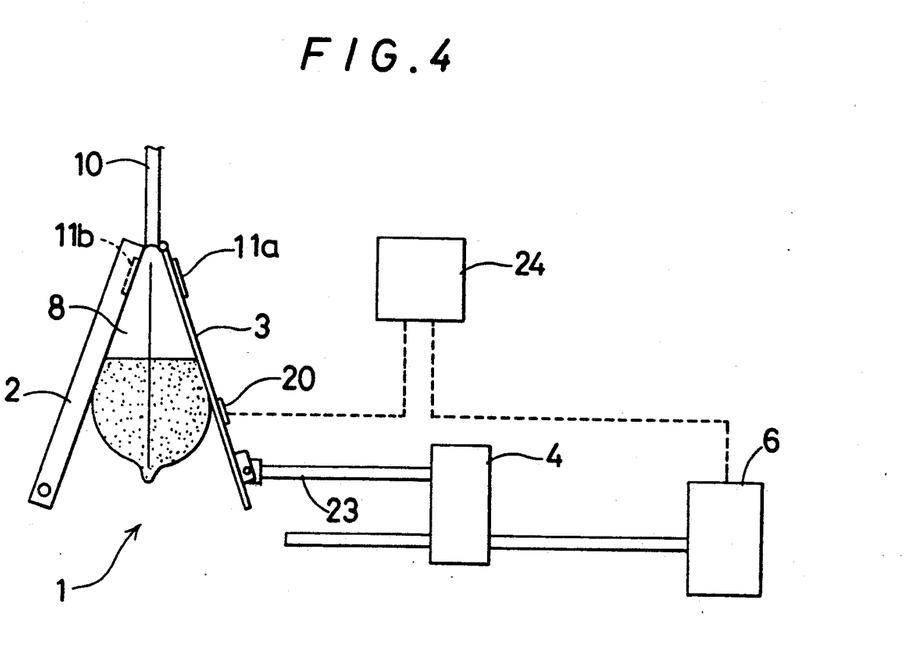
FIG. 4 is a schematic view of a liquid separator according to another embodiment of the present invention.

Next, a liquid separator of an embodiment shown in FIG. 4 will be described.

This liquid separator 1 comprises a first plate member 2, a second plate member 3 forming a receiving portion between it and the first plate member 2 for receiving a flexible liquid container 8 including liquid separated into the upper liquid layer and the lower liquid layer, and pushing means for pushing the second plate member 3 toward the first plate member 2, said pushing means automatically pushing the second plate member 3 at gradually decreasing speed after starting the discharge of the upper liquid layer from the flexible liquid container 8.

Specifically, the pushing means comprises a pushing member 4 for pushing the second plate member 3, drive means 6 for driving the pushing member 4, detecting means 20 for detecting the state of compression of the liquid container 8, and a drive means controller 24 for outputting a drive signal to the drive means 6 on the basis of a signal from the detecting means 20. The drive means controller 24 outputs a signal to the drive means 6 for gradually decreasing the pushing speed when receiving a detection signal from the detecting means 20 informing that the state in which the upper liquid layer is discharged from the liquid container 8 is detected.

The detecting means 20 is attached to a surface of the second plate member 3 to come into contact with the liquid container 8. The detecting means 20 may consist of a pressure sensor, an optical sensor for detecting the lower liquid layer in the liquid container 8, or an ultrasonic sensor. The detecting means 20 outputs a detection signal to the drive means controller 24 when it detects the state that the upper liquid layer is discharged from the liquid container 8 through a tube 10 due to the compression by the first and second plate members 2 and 3.

The first and second plate members 2 and 3 are provided with liquid detecting means 11a and 11b for detecting the lower liquid layer in the liquid container 8. When the lower liquid layer is detected by the liquid detecting means 11a and 11b, closing means (not shown) is operated to close the tube 10, completing the liquid separation operation.

The drive means 6 comprises, for example, a stepping motor. The pushing member 4 is moved toward the second plate member 3 by the drive means 6 so that a pushing rod 23 attached to the pushing member 4 pushes the second plate member 3.

Figure 5:
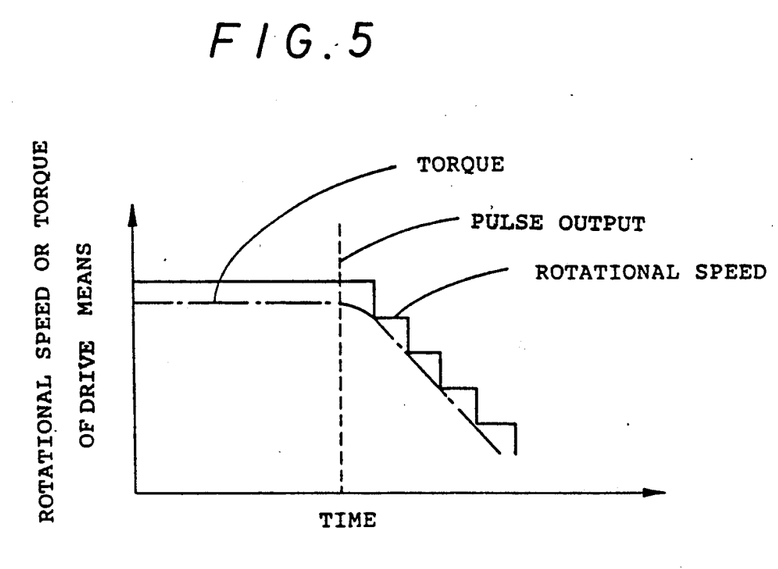
FIG. 5 is a graph showing the relationship between time and the rotational speed and the torque of the drive means of the embodiment of FIG. 4.

The drive means controller 24 outputs a signal to the drive means 6 for gradually decreasing the pushing speed when receiving a signal from the detecting means 20. More specifically, the drive means controller 24 outputs pulses for the stepping motor. The number of the pulses is decreased by a predetermined time. Thus, the rotational speed of the drive means 6 is decreased in accordance with the decrease of the pulses so that the advancing speed of the pushing member 4 and the pushing rod 23 is decreased as shown in FIG. 5. By this arrangement, the liquid container 8 is compressed slowly after the upper liquid layer starts to flow out of the liquid container 8. Thus, the upper liquid layer can be discharged from the liquid container 8 through the tube 10 without disturbing the boundary between the upper and lower liquid layers in the liquid container 8.

The detecting means 20 may not be provided. In that case, the drive means controller 24 can output a signal to the drive means 6 for gradually decreasing the pushing speed when the pushing member 4 reaches a predetermined position.

The pushing means may comprise the drive means 6 for pushing the second plate member 3, the detecting means 20 for detecting the state of compression of the flexible liquid container 8, and the drive means controller 24 for outputting a signal to the drive means 6 on the basis of a signal from the detecting means 20. The drive means controller 24 outputs a signal to the drive means 6 for gradually decreasing the pushing force when receiving a signal from the detecting means 20 informing that the state in which the upper liquid layer is discharged from the flexible liquid container 8 is detected.

The drive means controller 24 may output a signal to the drive means 6 for gradually decreasing the pushing force and speed. More specifically, the drive means controller 24 outputs pulses for the stepping motor of the drive means 6. The number of the pulses is decreased by a predetermined time. In addition, the voltage of the electric signal output from the drive means controller 24 to the stepping motor of the drive means 6 is decreased by a predetermined time. Thus, the rotational speed and the torque of the drive means 6 are decreased to decrease the speed of the pushing member 4 and the pushing rod 23 and to decrease the pushing force as shown in FIG. 5.

By this arrangement, the upper liquid layer can more efficiently be discharged from the liquid container 8 without disturbing the boundary between the upper and lower liquid layers in the liquid container 8.

The liquid container 8 is, for example, a blood bag which contains an anticoagulant liquid for collecting blood.

Specifically, the liquid container 8 is made of a flexible synthetic resin into a bag. The liquid container 8 is provided with a tube 10 which is in fluid communication with the interior of the liquid container 8. The tube 10 is made of a flexible synthetic resin such as flexible vinyl chloride and silicone resin like the liquid container 8. In this blood bag system, a plasma component container is connected to the other end of the tube 10. The tube 10 is provided with breakable communicating means for preventing the anticoagulant liquid in the blood bag from flowing into the plasma component container prior to blood collection.

EXAMPLE

Next, an example of an automatic liquid separator according to the present invention will be described.

Figure 6:
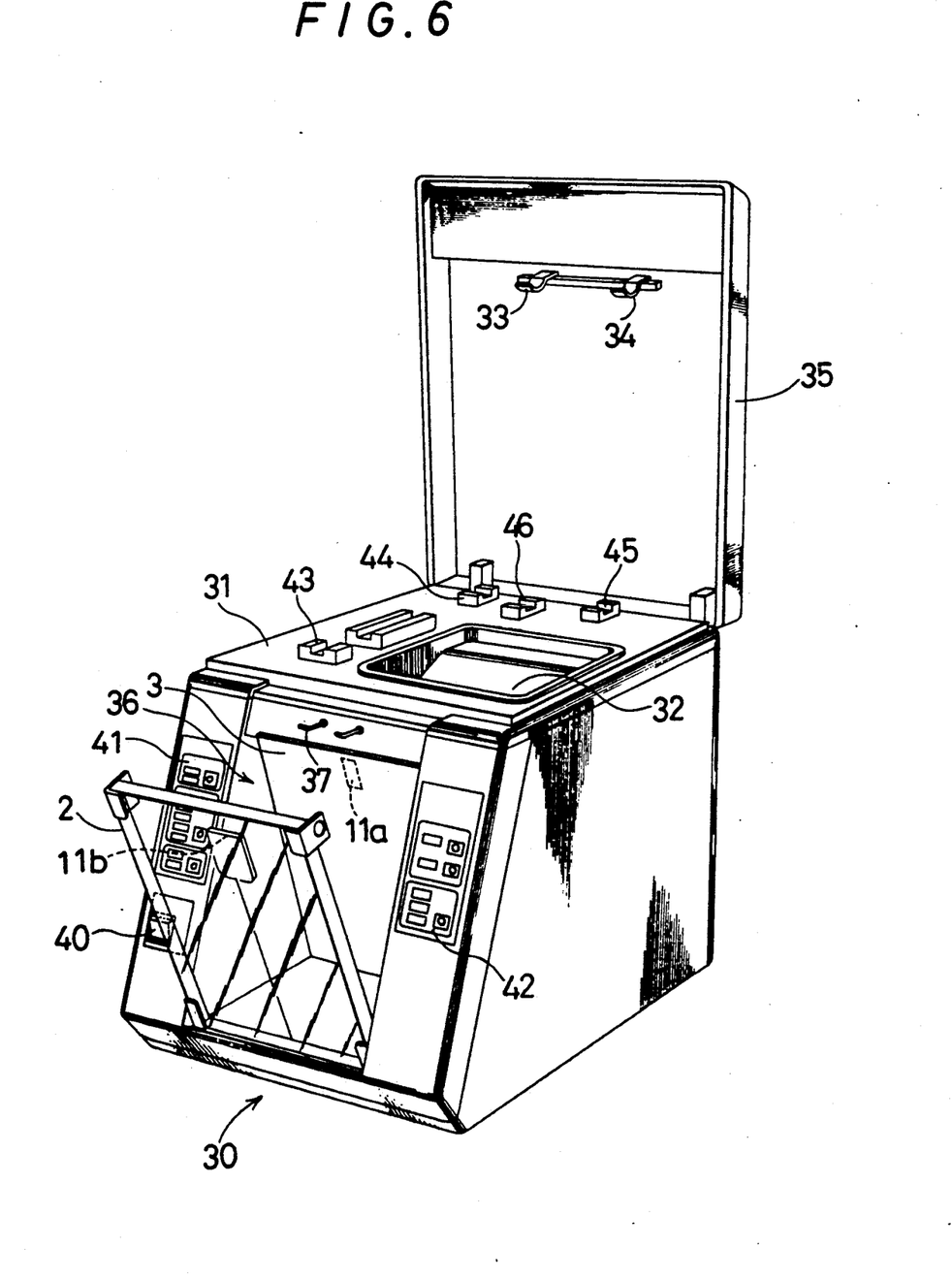
FIG. 6 is a perspective view of an embodiment in which a liquid separator of the present invention is applied to an automatic blood separator.
Figure 7:
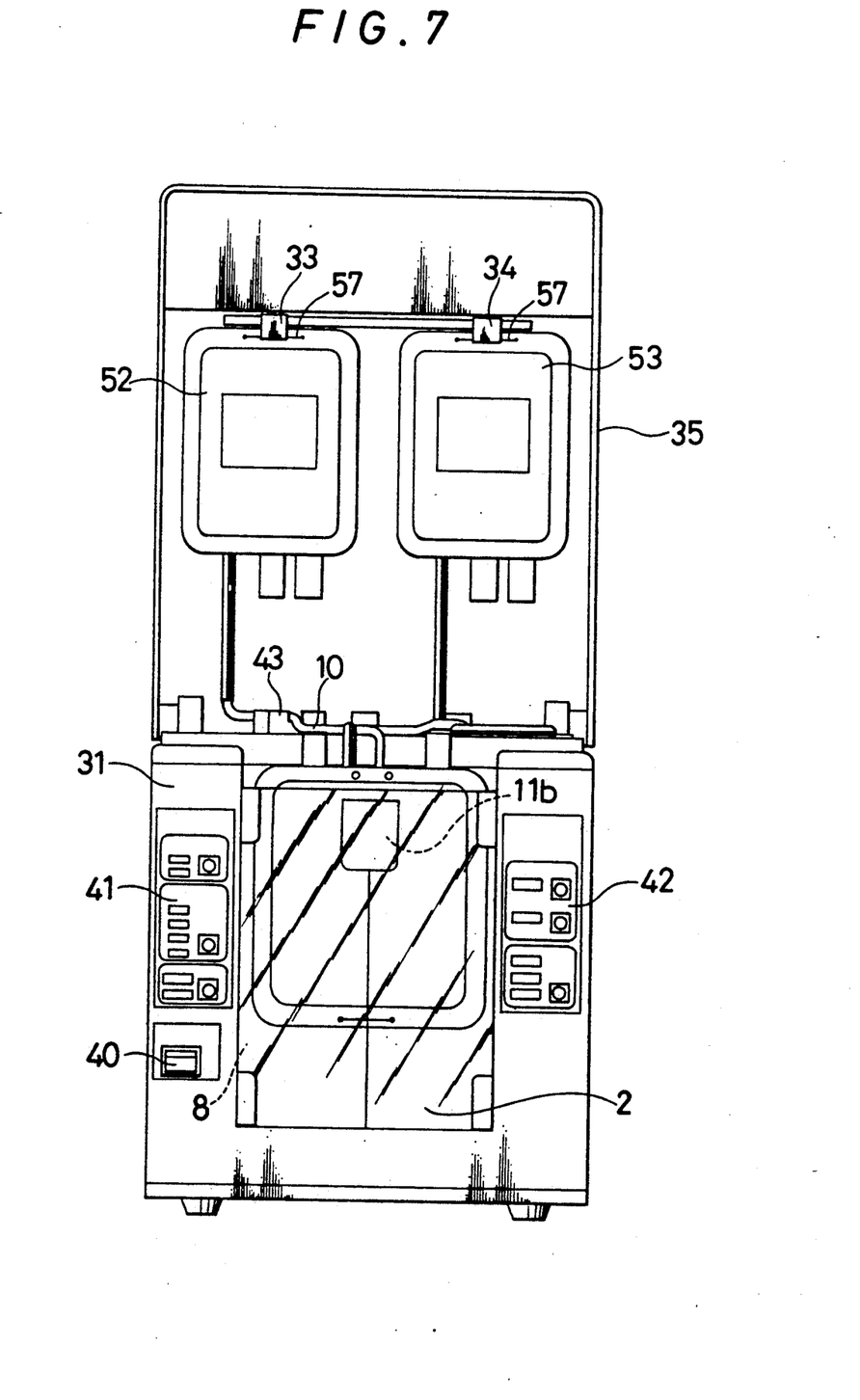
FIG. 7 is a front elevation of the blood separator of FIG. 6 in which quadruple blood bag is set.

FIG. 6 is a perspective view of an automatic blood separator 30. FIG. 7 is a front elevation in which a blood bag system is attached to the blood separator 30 of FIG. 6 and the first plate member 2 is set up and fixed.

Figure 8:
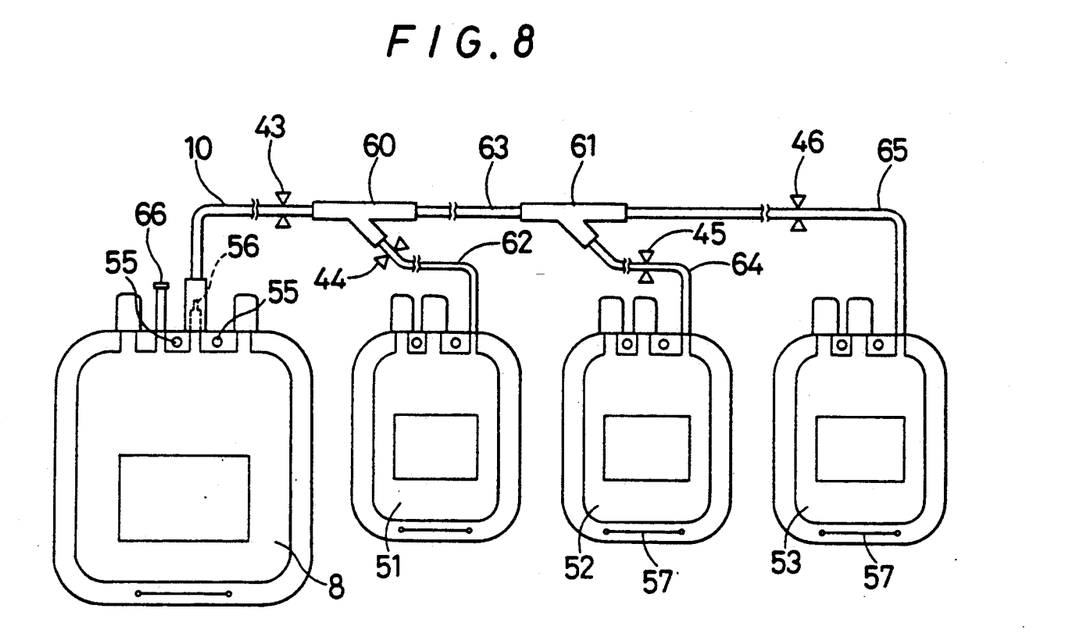
FIG. 8 is a view of the quadruple blood bag of FIG. 7.

The blood separator 30 can employ any type of blood bags of 200 ml and 400 ml. The blood separator 30 can also employ any of double blood bag, triple blood bag and quadruple blood bag. In this example, quadruple blood bag (400 ml) shown in FIG. 8 is employed. The quadruple blood bag comprises a main bag as the flexible liquid container 8, a first transfer bag 51, a second transfer bag 52 and a third transfer bag 53. The first to third transfer bags 51 to 53 are flexible bags like the main bag 8. A tube 10 is connected to the main bag 8. The tube 10 is provided with breakable communicating means 56. Holes 55 are formed in the upper portion of the main bag 8. The first transfer bag 51 is in fluid communication with the tube 10 through a branched tube 60 and a tube 62. Similarly, the second transfer bag 52 is in fluid communication with the tube 10 through the branched tube 60, a tube 63, a branched tube 61 and a tube 64. Further, the third transfer bag 53 is in fluid communication with the tube 10 through the branched tube 60, the tube 63, the branched tube 61 and a tube 65. All tubes are made of flexible synthetic resin.

A slit 57 is formed in each of the second and third transfer bags 52 and 53. After collecting blood in the main bag 8, a tube 66 used for the blood collection is closed and cut off. The quadruple blood bag has been centrifuged to separate blood in the main bag 8 into the upper liquid layer of plasma component, the intermediate layer of buffy coat layer including platelet and white blood cells, and the lower liquid layer of blood cell component.

The blood separator 30 comprises a housing 31 and a cover 35. The first plate member 2 is attached to the front portion of the housing 31 so as to be able to be opened and closed. The second plate member 3 is attached in the housing 31 at the rear of the first plate member 2. Above the second plate member 3 are disposed hooks 37 to be inserted in the holes 55 of the flexible liquid container (main bag) 8. The first and second plate members 2 and 3 are provided with liquid detecting means 11a and 11b, which are for detecting the boundary between the plasma layer and the buffy coat layer separated in the main bag 8 and the boundary between the buffy coat layer and the blood cell layer. The liquid detecting means 11a and 11b consist of, for example, a photosensor which detects the boundaries on the basis of the difference in absorbance, transmittance or reflectivity between the layers. A power switch 40 is disposed on the lower left side of the front surface of the housing 31. Control panels 41 and 42 including various control switches are disposed in the front surface of the housing 31. A main bag receiving portion 36 is formed between the first and second plate members 2 and 3. The first plate member 2 is open in FIG. 6 and the main bag 8 is put in the receiving portion 36 in this state and then the first plate member 2 is closed as shown in FIG. 7. In the housing 31 is disposed pushing means for pushing the second plate member 3 with gradually decreasing pressure after starting the discharge of the upper liquid layer from the main bag 8 as shown in FIG. 1. A receiving portion 32 for the first transfer bag 51 is formed in the upper surface of the housing 31 as shown in FIGS. 1 and 6. On the upper surface of the housing 31 are disposed a first tube clamper 43 for opening and closing the tube 10, a second tube clamper 44 for opening and closing the tube 62, a third tube clamper 45 for opening and closing the tube 64, and a fourth tube clamper 46 for opening and closing the tube 65 as shown in FIGS. 1, 6 and 8. Each tube clamper is driven by a solenoid connected to the tube clamper. A weight sensor 38 is disposed in a tray froming the receiving portion 32 as shown in FIG. 1. As shown in FIG. 7, hooks 33 and 34 are disposed on the cover 35. The second transfer bag 52 is hung by the hook 33 through the slit 57 formed in the bottom portion of the second transfer bag 52 and the third transfer bag 53 is hung by the hook 34 through the slit 57 formed in the bottom portion of the third transfer bag 53.

After setting each blood bag as shown in FIG. 7, the first plate member 2 is closed. When a separation start switch is turned on, the tube clampers 43 and 45 are open and the tube clampers 44 and 46 are closed. The communicating means 56 is then broken. The separation start switch is turned on again. The drive means then starts and the second plate member 3 is moved toward the first plate member 2. Then the upper liquid layer of plasma component flows from the main bag 8 into the second transfer bag 52 hung by the hook 33 through the tubes 10, 63 and 64. When the liquid detecting means 11a and 11b detect the boundary of red blood cell component, the tube clampers 43 and 45 are closed. Subsequently, the tube clampers 43 and 44 are opened. Then the plasma component, the buffy coat layer and the red blood cell component remaining in the main bag 8 flows in the first transfer bag 51 in this order through the tubes 10 and 62. When the weight sensor 38 disposed in the tray 32 receiving the first transfer bag 51 detects that the weight of the first transfer bag 51 reaches a first predetermined value, the tube clampers 43 and 44 are closed. Then the second plate member 3 is released from pushing and the first plate member 2 is opened. Subsequently, the tube clampers 44 and 45 are opened so that the plasma flows from the second transfer bag 52 into the first transfer bag 51. When the weight sensor 38 of the tray 32 detects that the weight of the first transfer bag 51 reaches a second predetermined value, the tube clampers 44 and 45 are closed.

A liquid separator of the present invention comprises a first plate member, a second plate member forming a receiving portion between it and said first plate member for receiving a flexible liquid container including liquid separated into the upper liquid layer and the lower liquid layer, and pushing means for pushing said second plate member toward said first plate member, said pushing means automatically pushing said second plate member with gradually decreasing pressure after starting the discharge of said upper liquid layer from said flexible liquid container. Therefore, the upper liquid layer can be discharged from the flexible liquid container without disturbing the boundary between the upper and lower liquid layers in the flexible liquid container. Thus, the upper liquid layer can automatically and efficiently be taken out from the flexible liquid container without mixing with the lower liquid layer and without any complicated and troublesome manipulation. If the discharge of the upper liquid layer is automatically stopped with a sensor detecting the boundary between the upper and lower liquid layers, it is possible to decrease errors of the sensor caused by the disturbance of the boundary.

A liquid separator of the present invention comprises a first plate member, a second plate member forming a receiving portion between it and said first plate member for receiving a flexible liquid container including liquid separated into the upper liquid layer and the lower liquid layer, and pushing means for pushing said second plate member toward said first plate member, said pushing means automatically pushing said second plate member at gradually decreasing speed after starting the discharge of said upper liquid layer from said flexible liquid container. Therefore, the upper liquid layer can be discharged from the flexible liquid container without disturbing the boundary between the upper and lower liquid layers in the flexible liquid container. Thus, the upper liquid layer can automatically and efficiently be taken out from the flexible liquid container without mixing with the lower liquid layer and without any complicated and troublesome manipulation. If the discharge of the upper liquid layer is automatically stopped with a sensor detecting the boundary between the upper and lower liquid layers, it is possible to decrease errors of the sensor caused by the disturbance of the boundary.

We claim:

1. A liquid separator comprising:
   a first plate member,
   a second plate member spaced from said first plate member and forming a receiving portion between said second plate member and said first plate member for receiving a flexible liquid container in said receiving portion, said flexible liquid container including liquid separated into an upper liquid layer and a lower liquid layer, and
   pushing means for pushing said second plate member toward said first plate member, said pushing means automatically pushing said second plate member with gradually decreasing pressure after starting of a discharge of said upper liquid layer from said flexible liquid container,
   said pushing means comprising a pushing member, a spring member disposed between said pushing member and said second plate member, a shaft member inserted in said spring member and movably penetrating said pushing member, and drive means for driving said pushing member toward said second plate member, said second plate member being pushed through said spring member, and
   wherein said pushing means is arranged such that a distance between upper end portions of said first and second plate members is kept substantially constant, and said second plate member is rotated toward said first plate member around an axis positioned in said upper end portion of said second plate member.

2. A liquid separator according to claim 1, further comprising liquid detecting means for detecting said lower liquid layer in said flexible liquid container, said liquid detecting means being disposed in an upper portion of said receiving portion for said flexible liquid container.

3. A liquid separator according to claim 1, wherein said flexible liquid container is a blood bag.

4. A liquid separator according to claim 1, wherein said drive means of said pushing means automatically stops driving said pushing member after said second plate member is pushed until the discharge of said upper liquid layer from said flexible liquid container starts, and subsequently, said second plate member is pushed by the restoring force of said spring member compressed by said pushing member and said second plate member so that said second plate member is pushed with gradually decreasing pressure.

5. A liquid separator according to claim 1, wherein said drive means of said pushing means automatically stops driving said pushing member after said second plate member is pushed until the distance between said first and second plate members reaches a predetermined value, and subsequently, said second plate member is pushed by the restoring force of said spring member compressed by said pushing member and said second plate member so that said second plate member is pushed with gradually decreasing pressure.

6. A liquid separator according to claim 1, further comprising liquid detecting means for detecting a boundary between said upper and lower liquid layers in said flexible liquid container, said liquid detecting means being disposed in an upper portion of said receiving portion for said flexible liquid container.

7. A liquid separator comprising:
   a first plate member,
   a second plate member spaced from said first plate member and forming a receiving portion between said second plate member and said first plate member for receiving a flexible liquid container in said receiving portion, said flexible liquid container including liquid separated into an upper liquid layer and a lower liquid layer, and
   pushing means for pushing said second plate member toward said first plate member, said pushing means comprising drive means for pushing said second plate member, detecting means for detecting a state of compression of said flexible liquid container, and a drive means controller for outputting a drive signal to said drive means on the basis of a signal from said detecting means, said drive means controller outputting said drive signal to said drive means for gradually decreasing the pushing force of said drive means responsive to receiving said signal from said detecting means informing of detecting of a state that said upper liquid layer is discharged from said flexible liquid container, and wherein said pushing means is arranged such that a distance between upper end portions of said first and second plate members is kept substantially constant, and said second plate member is rotated toward said first plate member around an axis positioned in said upper end portion of said second plate member.

8. A liquid separator according to claim 7, wherein said drive means controller outputs said drive signal to said drive means for gradually decreasing the pushing force and speed of said drive means responsive to receiving said signal from said detecting means informing or detecting of a state that said upper liquid layer is discharged from said flexible liquid container.

9. A liquid separator according to claim 7, wherein said flexible liquid container is a blood bag.

10. A liquid separator comprising:
a first plate member,
a second plate member spaced from said first plate member and forming a receiving portion between said second plate member and said first plate member for receiving a flexible liquid container in said receiving portion, said flexible liquid container including liquid separated into an upper liquid layer and a lower liquid layer, and
pushing means for pushing said second plate member toward said first plate member,
said pushing means comprising drive means for pushing said second plate member, detecting means for detecting a state of compression of said flexible liquid container, and a drive means controller for outputting a drive signal to said drive means on the basis of a signal from said detecting means, said drive means controller outputting said drive signal to said drive means gradually decreasing the pushing speed of said drive means responsive to receiving said signal from said detecting means informing of detecting of state that said upper liquid layer is dsicharged from said flexible liquid container, and wherein said pushing means is arranged such that a distance between upper end portions of said first and second plate members is kept substantially constant, and said second plate member is rotated toward said first plate member around an axis positioned in said upper end portion of said second plate member.

11. A liquid separator according to claim 10, wherein said drive means controller outputs said drive signal to said drive means for gradually decreasing the pushing force and speed of said drive means responsive to receiving said signal from said detecting means informing of detecting of a state that said upper liquid layer is discharged from said flexible container.

12. A liquid separator according to claim 10, wherein said flexible liquid container is a blood bag.

13. A liquid separator comprising:
a first plate member,
a second plate member spaced from said first plate member and forming a receiving portion between said second plate member and said first plate member for receiving a flexible liquid container in said receiving portion, said flexible liquid container including liquid separated into an upper liquid layer and a lower liquid layer, and
pushing means for pushing said second plate member toward said first plate member, said pushing means automatically pushing said second plate member with gradually decreasing pressure after starting of a discharge of said upper liquid layer from said flexiblee liquid container,
said pushing means comprising a pushing member, a spring member disposed between said pushing member and said second plate member, a shaft member inserted in said spring member and movably penetrating said pushing member, and drive means for driving said pushing member toward said second plate member, said second plate member being pushed through said spring member, and wherein the distance between upper portions of said first and second plate members is kept substantially constant when said liquid container is compressed, and said second plate member is pivotally supported at its upper end portion and is rotated toward said first plate member to compress said liquid container from the upper portion to the lower portion.

14. A liquid separator according to claim 13, wherein said drive means of said pushing means automatically stops driving said pushing member after said second plate member is pushed until the discharge of said upper liquid layer from said flexible liquid container starts, and subsequently, said second plate member is pushed by the restoring force of said spring member compressed by said pushing member and said second plate member so that said second plate member is pushed with gradually decreasing pressure.

15. A liquid separator according to claim 13, wherein said drive means of said pushing means automatically stops driving said pushing member after said second plate member is pushed until the distance between said first and second plate members reaches a predetermined value, and subsequentially, said second plate member is pushed by the restoring force of said spring member compressed by said pushing member and said second plate member so that said second plate member is pushed with gradually decreasing pressure.

16. A liquid separator to claim 13, further comprising liquid detecting means for detecting a boundary between said upper and lower liquid layers in said flexible liquid container, said liquid detecting means being disposed in an upper portion of said receiving portion for said flexible liquid container.

* * * * *